United States Patent [19]
Bertolini et al.

[11] Patent Number: 6,093,324
[45] Date of Patent: Jul. 25, 2000

[54] PURIFICATION OF IMMUNOGLOBULINS

[75] Inventors: Joseph Bertolini, Ashburton; Jeffrey Raymond Davies, Ivanhoe; John Wu, Coburg; Germano Coppola, Croydon, all of Australia

[73] Assignee: CSL Limited, Victoria, Australia

[21] Appl. No.: 09/242,028

[22] PCT Filed: Aug. 7, 1997

[86] PCT No.: PCT/AU97/00498

§ 371 Date: Feb. 24, 1999

§ 102(e) Date: Feb. 24, 1999

[87] PCT Pub. No.: WO98/05686

PCT Pub. Date: Feb. 12, 1998

[30] Foreign Application Priority Data

Aug. 7, 1996 [AU] Australia .................. PO 1468
May 8, 1997 [AU] Australia .................. PO 6688

[51] Int. Cl.[7] .................................... B01D 15/08
[52] U.S. Cl. .................. 210/635; 210/656; 210/198.2; 530/387.1; 530/413; 530/416
[58] Field of Search ................ 210/635, 656, 210/198.2, 502.1; 530/387.1, 413, 416, 417

[56] References Cited

U.S. PATENT DOCUMENTS

| | | | |
|---|---|---|---|
| 4,845,199 | 7/1989 | Hirao et al. | 530/387 |
| 4,849,508 | 7/1989 | Magnin et al. | 530/387 |
| 5,552,041 | 9/1996 | Afeyan | 210/198.2 |
| 5,679,260 | 10/1997 | Boos | 210/723 |

FOREIGN PATENT DOCUMENTS

| | | | |
|---|---|---|---|
| 1 201 063 | 2/1986 | Canada | 210/635 |
| 0 035 204 A2 | 9/1981 | European Pat. Off. | 210/635 |
| 0 605 219 A1 | 7/1994 | European Pat. Off. | 210/635 |
| 0 679 728 A2 | 11/1995 | European Pat. Off. | 210/635 |
| WO 86/06727 | 11/1986 | WIPO | 210/635 |

OTHER PUBLICATIONS

Journal of Chromatographya vol. 743 No. 1 Dated 1996 pp. 171–180 Yan Yan–Bo et al. "Influence of column type and chromatographic conditions on the ion–exchange chromatography of immunoglubulins".

Biotechnology of Blood Proteins vol. 227 Dated: 1993 pp. 207–212 Nourichafi N et al.; "Comparison of various chromatographic supports for purifying human plasmatic immunoglobulins from Cohn II & III fraction".

Journal of Chromatography vol. 590 Dated 1992 pp. 255–261 Neidhardt, Edith et al., "Rapid, two–step purification process for the preparation of pyrogen–free murine immunglobulin G1 monoclonal antibodies".

*Primary Examiner*—Ernest G. Therkorn
*Attorney, Agent, or Firm*—Nixon & Vanderhye

[57] ABSTRACT

A method for the purification or recovery of immunoglobulins from plasma or other immunoglobulin-containing material is disclosed which includes subjecting the plasma or other immunoglobulin-containing material to chromatographic fractionation on a macroporous anion-exchange resin to recover an immunoglobulin-containing fraction therefrom.

20 Claims, 8 Drawing Sheets

PURIFICATION OF IMMUNOGLOBULINS

REFERENCE TO RELATED APPLICATIONS

This application is a 371 of PCT/AU97/00498 filed Aug. 7, 1997.

FIELD OF THE INVENTION

This invention relates to the purification of immunoglobulins from immunoglobulin-containing material, and particularly but not exclusively to the purification of immunoglobulins from plasma and plasma fractions. A particular objective of the present invention is the purification of immunoglobulins to provide a product which is suitable for intravenous administration to humans.

BACKGROUND OF THE INVENTION

Immunoglobulins derived from human plasma are used in the treatment of a number of clinical conditions such as primary agammaglobulinaemia, ITP and Kawasaki Syndrome. There is a growing demand for the product as an increasing number of studies are finding that it has application in many other autoimmune conditions. At present, immunoglobulins are purified from plasma by the Cohn fractionation procedure which separates plasma proteins by differential precipitation with ethanol. (Cohn et al., 1946).

The Cohn fractionation process has a number of disadvantages:

1. it is not amenable to automation;
2. it utilises a potentially hazardous chemical, ethanol, which impacts on plant design;
3. it exposes the immunoglobulins to harsh conditions which may affect the function of antibodies; and
4. the yield of immunoglobulins is relatively low (~40%).

Therefore, there is a need for an efficient process for the recovery of immunoglobulins (IgG) at large scale.

A number of chromatographic processes for the production of pure IgG for intravenous administration have been described. Initially, ion-exchange resins such as DEAE-Sephadex were employed largely for "clean-up" purposes such as the removal of aggregates from Cohn fractionation derived product (Björling, 1972; Hoppe et al. 1973). However, integrated chromatographic processes for the recovery of IgG from plasma were subsequently described. Condie described a chromatographic process yielding IgG which was safe for injection (Condie, 1979; Condie 1980). One of the major issues that needed to be addressed was the potential fouling of resins by lipoproteins present in plasma. In this process, fumed colloidal silica (Aerosil) was used to remove lipoprotein from plasma prior to the chromatographic fractionation. However this treatment resulted in a marked decrease of IgG3 subclass under the chosen conditions. This altered subclass distribution is clinically undesirable in an immunoglobulin preparation. Further, removal of the silica was effected by centrifugation which is not amenable to the processing of large batches of immunoglobulin source material. The subsequent ion-exchange chromatography step was carried out using a QAE-Sephadex column at pH 7.0 with imidazole-acetate buffer at an ionic strength of 6.15 mS. Under these conditions, it would be anticipated that there would be increased interaction between immunoglobulin and the resin leading to reduced recovery. In particular, there would be losses of IgG3 and IgG4 which have a relatively anodal charge relative to IgG1 and IgG2. In addition, the use of imidazole-containing buffers or other buffers required to perform the process at pH 7 would significantly add to costs.

Björling has presented a procedure for isolation of gamma globulin from defibrinated serum by ion-exchange chromatography on CM-Sepharose CL6B followed by DEAE-Sepharose CL6B (Björling, 1985). However, in both these cases the anion-exchange step is carried out at or near pH 7.0, which would be undesirable, as described above. The use of a cation-exchange step under conditions where IgG is bound would require the use of more cycles than if anion-exchange resin was used under conditions where only contaminating proteins are bound. The binding of IgG with the use of cation-exchange chromatography would also result in greater loss of material than with the use of anion-exchange chromatography under conditions where contaminating proteins are retained and immunglobulins are unbound.

Anion-exchange chromatography has also been performed on DEAE-Trisacryl at pH 8.4 (Tousch et al 1989). Under these conditions it would not be applicable to use plasma or plasma fractions such as Cohn Supernatant 1 (SNI) as all proteins would bind thus limiting the effective capacity and through-put. Therefore partial purification by Cohn fractionation was initially performed to remove albumin. Under these chromatographic conditions there would be binding of IgG to the resin. This would most likely result in reduced recovery of protein and compromised sub-class distribution.

Friesen and co-workers described a process for the purification of immunoglobulin (IVIG) using anion exchange at lower pH values. Thus, plasma cryoprecipitate was applied onto DEAE-Sepharose CL6B at pH 5.2, followed by DEAE-Biogel at pH 6.5 or DEAE-Sephadex A-50 at pH 7.5. (Friesen et al. 1985; Friesen, 1982). The DEAE-Sepharose and DEAE-Biogel steps were however carried out in 70 mM and 20 mM acetate respectively, and at pH 5.2 and 6.0. In the light of data presented herein, these buffers do not represent optimal conditions for chromatographic purification of immunoglobulin.

Berglöf and co-workers later incorporated Fast Flow Sepharose supports in their process, using the sequence DEAE-Sepharose-FF, Q-Sepharose FF, CM-Sepharose FF (Berglöf and Eriksson 1989). This process has lwow capacity capabilities reflecting the less than optimal configuration of the process.

Another process involving ion-exchange chromatography for purifying an immune serum globulin fraction from crude plasma (Samo, 1991) employs cation exchange on CM-Sepharose FF at pH 5–6, followed by anion exchange on DEAE-Sepharose FF at pH 7.0–8.5. The process however requires an initial PEG+solvent/detergent clean-up step of the Cohn fraction I+II+III starting material. Furthermore, it would be expected that the high pH in the anion-exchange step would result in losses of IgG through adsorption to the resin.

The processes described above therefore incorporate many undesirable features. These include the following:

a. Cohn fractionation is used in most of these processes to separate albumin from immunoglobulins. This prevents the development of an integrated completely chromatographic process. The precipitation of the immunoglobulin fraction followed by resuspension would also result in greater loss of IgG when compared to a process which avoids the need to have a preliminary immunoglobulin enrichment step.

b. The use of cation-exchange chromatography involving conditions which promote binding of immunoglobulins would limit the through-put of the process. It would also be expected that IgG recovery would be reduced and there could be selective depletion of immunoglobulin sub-classes which could limit the clinical acceptance of the product.

c. Where anion-exchange chromatography has been used, conditions of pH have been chosen which have led to sub-class depletion.

d. In none of the processes is there recognition that the degree of loading of the resin can affect the IgM content of the recovered product—an important parameter in defining the clinical usefulness of the final product.

e. Processes exist where plasma has been used directly as the starting material for fractionation, however this is undesirable, as lipoprotein content can promote column fouling.

f. None of the processes have recognised the advantage of macro-porous resins for the production of purified immunoglobulins.

In the work leading to the present invention, it has been found that chromatographic processes for the purification of immunoglobulins from plasma and other immunoglobulin-containing materials can be enhanced by use of a macro-porous anion-exchange resin. In addition, where the starting material contains lipoproteins, the purification processes can also be enhanced by introducing a pretreatment step wherein lipoproteins are removed by adsorption prior to application of the starting material onto the chromatography column.

SUMMARY OF THE INVENTION

Accordingly, the present invention provides a method for the purification or recovery of immunoglobulins from plasma or other immunoglobulin-containing material, which comprises the step of:

subjecting the plasma or other immunoglobulin-containing material to chromatographic fractionation on a macro-porous anion-exchange resin to recover an immunoglobulin-containing fraction therefrom.

Where the starting material is plasma or other immunoglobulin-containing material which contains lipoproteins, the method of the invention preferably includes a pretreatment step wherein lipoproteins are removed by adsorption prior to the chromatographic fractionation step.

Optionally, and preferably, viral inactivation of the recovered product is effected, for example by subjecting the immunoglobulin-containing fraction to pasteurisation.

DETAILED DESCRIPTION OF THE INVENTION

Particularly preferred starting materials for use in the method of the present invention are plasma, or plasma fractions obtained by the Cohn fractionation process, such as Cohn Supernatant I (fibrinogen depleted plasma) or solubilised and clarified action II+III.

Where the starting material is plasma or other immunoglobulin-containing material containing lipoproteins, such as Supernatant I, the lipoproteins are preferably removed from the starting material by adsorption under appropriate conditions to void or minimise the loss of immunoglobulin or of specific sub-classes thereof. A particularly preferred adsorbent material for use in accordance with the present invention is a finely divided silicon dioxide (silica) adsorbent such as Aerosil, for example having a particle size in the range of from 5–50 nm. Whilst the use of Aerosil or other divided silica adsorbent can result in the loss of immunoglobulin or of specific subclasses, conditions pH and of ionic strength have been identified which maximise recovery.

Removal of lipoproteins in accordance with this aspect of the present invention prior to chromatographic fractionation of the plasma or other starting material prevents column fouling due to the accumulation of adsorbed lipoproteins.

The choice of the appropriate grade of Aerosil allows the use of filtration in preference to centrifugation for the recovery of delipidated material and renders the process amenable for large scale application. In addition, the use of Aerosil in combination with a filter aid such as Diacel, assists in the recovery of delipidated material by filtration. This greatly facilitates the application of the method to the processing of large volumes of material.

In accordance with a further preferred feature of the present invention, the chromatographic fractionation of the delipidated material prepared as described above may comprise the further steps of:

fractionation of the delipidated material by anion-exchange chromatography to produce a first immunoglobulin-containing fraction; and purification of the first immunoglobulin-containing fraction by a second anion-exchange chromatographic step using a macro-porous anion-exchange resin.

In accordance with this chromatographic fractionation procedure, the delipidated starting material is firstly fractionated by anion-exchange chromatography under conditions of pH and ionic strength which generate a partially purified preparation which is amenable further purification by anion-exchange chromatography.

Preferably, the delipidated material is diafiltered, pH adjusted and euglobulin depleted prior to fractionation by anion-exchange chromatography using DEAE-Sepharose FF under conditions of loading, pH and ionic strength which maximise the purity of immunoglobulin (crude IgG) obtained at this step. In particular, these conditions ensure the maximal separation of transferrin from immunoglobulins even though the physico-chemical properties of transferrin closely approximate those of immunoglobulins. The generation of a relatively pure immunoglobulin preparation at this step is important to the overall process as it facilitates the subsequent use of a second anion-exchange step to generate the pure final product under conditions of pH which ensure that the loading capacity of the resin is adequate for a practical commercial process and that subclass recovery is appropriate.

The second anion-exchange chromatographic step comprises purification of the immunoglobulin-containing fraction with macro-porous anion-exchange resins under conditions of loading, ionic strength and pH which generate a highly purified product with intact sub-class distribution, low IgA and IgM concentration and anti-A and anti-B levels within accepted pharmacopoeidial limits. The availability of an immunoglobulin-containing fraction significantly depleted of contaminating proteins, in particular transferrin, renders this approach practical. Furthermore, conditions of resin type, pH, conductivity, temperature, total loading and protein concentration of loaded solution have been identified which ensure a practical process that generates a clinically acceptable product. Specifically, the use of macro-porous resins with a pore size of greater than 1000 Å (such as Macro-Prep HQ, MacroPrep Q, Poros HQ, Q Hyper DM) is preferred to achieve a high adsorptive capacity for contaminating proteins (especially transferrin). Other non-macroporous resins exhibit lower capacities which may impact on the practicality of the chromatographic process.

Thus, in one aspect, the present invention provides a chromatographic process for commercially recovering a clinically useful immunoglobulin preparation from plasma or Supernatant I (fibrinogen depleted plasma).

It has been recognised that delipidation of these materials is required prior to chromatographic fractionation in order to prevent column fouling due to the accumulation of adsorbed lipoproteins. This is preferably achieved by the use of a finely divided silica adsorbent, preferably having a particle size of 5–50 nm, such as Aerosil, particularly Aerosil 200 or Aerosil 380. The use of Aerosil can result in the loss of immunoglobulin or of specific sub-classes, however, conditions of ionic strength have been identified which maximise recovery. Furthermore, conditions have been identified which allow the process to incorporate filtration to recover delipidated immunoglobulin-containing material which makes the process amenable to large-scale application. Preferably, the delipidation step is performed at a pH in the range 5.2–7.2 and at a conductivity of between 6 and 12 mS/cm. The delipidation is preferably carried out using Aerosil 380 adsorbent. Preferably also, a filter aid such as Diacel is used in combination with the Aerosil adsorbent.

As previously described, the delipidated material may be diafiltered, pH adjusted and euglobulin depleted prior to fractionation by anion-exchange chromatography (for example on DEAE-Sepharose FF). Conditions of loading pH and ionic strength have been identified which maximise the purity of immunoglobulin (crude IgG) obtained at this step. The generation of a relatively pure immunoglobulin preparation at this step is integral to the process as it facilitates the subsequent use of a second anion-exchange step to generate the pure final product under conditions of pH which ensures that the loading capacity of the resin is adequate for a practical process without compromising subclass distribution. Preferably, fractionation of the delipidated, euglobulin-depleted material is effected on a DEAE-Sepharose FF column at pH 5.2 and at a conductivity of 0.5–1.0 mS/cm.

The immunoglobulin preparation generated from the first anion-exchange step is subjected to final purification by passage through a second anion-exchange column of macro-porous anion-exchange resin. It has been found that the use of macroporous resins with a pore size of greater than 1000 Å (such as Macro Prep HQ, Macro Prep Q, Porous HQ, Q Hyper DM, Hyper D HQ) at pH of 6.0–6.6, preferably about 6.5, provides adequate adsorptive capacity for contaminating proteins. Other non-macroporous resins exhibit unacceptably low capacity for contaminating proteins. At significantly less than pH 6.2, even macroporous resins exhibit a diminished binding capacity for contaminating proteins present in the crude immunoglobulin preparation derived from the initial fraction by anion-exchange chromatography. At significantly higher pH, there is a progressive depletion of subclass $IgG_4$. It has also been found that the amount of crude IgG loaded onto the second anion-exchange column determines the IgM content of the final product. An appropriate level of loading has therefore been identified to minimise IgM flow-through. Conditions of temperature and concentration of the crude IgG solution at which loading is performed, have also been identified to maximise the capacity of the resin for transferrin-the major contaminating protein in the crude IgG preparation. Preferably, in purification of immunoglobulin from the crude IgG preparation, the macro-porous resin is equilibrated in buffer of pH 6.0–6.6 and conductivity 0.7–1.5 mS/cm. In this purification step, the crude IgG preparation is preferably also adjusted to pH 6.0 to 6.6 and conductivity maintained between 0.7 and 1.5 mS/cm. Preferably also, the purification is undertaken at a temperature between 4 and 20° C., using a protein concentration of less than about 3 mg/ml and with a loading of crude IgG preparation not exceeding about 50 mg of protein per mL of resin.

In another aspect of the invention, where the starting material is resolubilised Fraction II+III or other immunoglobulin-containing material which is already lipoprotein-depleted and partially purified, the material is simply subjected to final purification by passage through the column of macro-porous anion-exchange resin as described above.

Preferably, the final purified IgG product is subjected to viral inactivation, for example by pasteurisation of the product at 60° C. for 10 hours, preferably in the presence of a stabiliser, at a protein concentration of not more than 3%.

Further features of the present invention are more fully described in the following Example(s). It is to be understood, however, that this detailed description is included solely for the purposes of exemplifying the present invention, and should not be understood in any way as a restriction on the broad description of the invention as set out above.

BRIEF DESCRIPTION OF THE DRAWINGS

FIG. 8 shows the effect of the protein concentration of the crude IgG preparation loaded onto Macro-Prep HQ on transferrin flow-through; and FIG. 9 shows the effect of the degree of loading of crude IgG onto Macro-Prep HQ on IgM flow-through.

DESCRIPTION OF THE PREFERRED EMBODIMENTS

EXAMPLE 1

Figure 1:
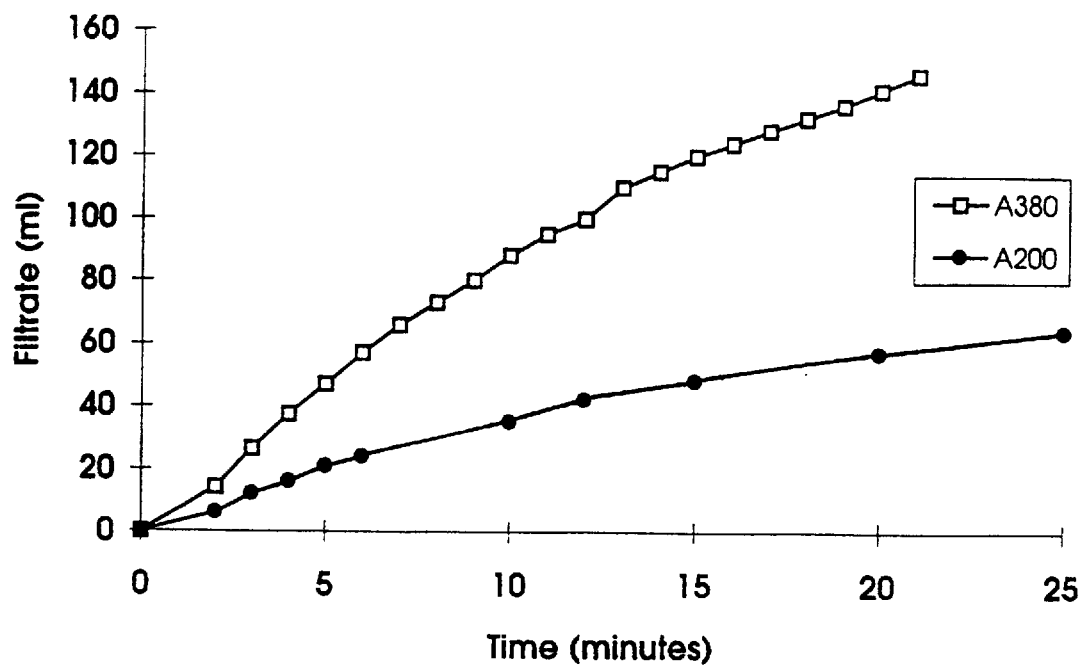
FIG. 1 is a comparison of the filterability of Supernatant I by leaf-filtration through beds composed of Diacel filter-aid and Aerosil 200 or Aerosil 380.

The use of Aerosil for delipidation of immunoglobulin-containing material such as Cohn Supernatant I has been investigated as described below.

a. Table I illustrates the ability of Aerosil 200 to adsorb lipoproteins from Supernatant I. Aerosil 200 was added to Supernatant I at various ratios of total protein. After mixing for 30 minutes at 4° C., delipidated supernatant was recovered by centrifugation. The major lipoprotein component of plasma, Apolipoprotein A, was quantitated by nephelometry or immunoelectrophoresis. It can be seen that increasing amounts of Aerosil result in increased removal of lipoproteins and that removal is promoted at pH 5.2. The conductivity of the Supernatant I is 9.0 mS/cm.

TABLE 1

The Effect Of Aerosil 200 Concentration On Lipoprotein Removal From Supernatant I.

| Aerosil | Apolipoprotein A (mg/mL)* | | Apolipoprotein A (mg/ml)+ | |
| --- | --- | --- | --- | --- |
| Conc. | pH 7.2 | pH 5.2 | pH 7.2 | pH 5.2 |
| No Aerosil | 1.04 | 0.99 | 1.65 | 0.84 |
| 50 mg/g protein | 0.90 | 0.67 | — | — |
| 100 mg/g protein | 0.64 | 0.30 | — | — |
| 150 mg/g protein | 0.42 | 0.25 | 0.7 | 0.09 |
| 200 mg/g protein | 0.29 | 0.25 | 0.36 | 0.03 |
| 250 mg/g protein | 0.25 | 0.25 | 0.085 | 0.02 |

Apolipoprotein A was measured by nephelometry * or by immunoelectrophoresis+

Under the conditions described above, exposure of Supernatant I to less than 200 mg Aerosil 200/g protein present in Supernatant I results in less than 5% loss of immunoglobulins. At 250 mg Aerosil/g protein an approximately 10% loss was observed.

b. Table 2 shows that recovery of immunoglobulins following exposure of Supernatant I to Aerosil 200 is a function of ionic strength. Supernatant I was dialysed at 4° C. to achieve the conductivities indicated, following pH adjustment and centrifugation to effect clarification, Aerosil 200 and Diacel 150 at 0.18 g/g protein and 0.3 g/g protein was added respectively. Following mixing for 30 minutes, the mixture was centrifuged and immunoglobulin concentration measured in the supernatant by nephelometry.

TABLE 2

The Effect Of Conductivity and pH on IgG Recovery Following Aerosil Treatment Of Supernatant I.
IgG (mg/mL)

| pH | Cond. (mS/cm) | Initial | After Clarification By Centrifugation | % | After Aerosil Extraction | % |
| --- | --- | --- | --- | --- | --- | --- |
| 7.2 | 9.0 | 5.62 | 5.81 | 100 | 5.81 | 100 |
|  | 1.2 | 4.34 | 4.35 | 100 | 2.59 | 60 |
|  | 0.6 | 4.47 | 4.03 | 90 | 2.31 | 52 |
| 5.2 | 9.0 | 5.59 | 5.40 | 97 | 5.27 | 94 |
|  | 1.6 | 3.95 | 4.00 | 100 | 3.7 | 94 |
|  | 0.8 | 4.21 | 3.78 | 90 | 3.40 | 81 |

Losses of IgG increased markedly at lower ionic strengths. This was attenuated if the Aerosil extraction was performed at pH 5.2.

b Table 3 illustrates the effect of Aerosil 200 exposure on subclass distribution. At levels greater than 200 mg/g protein there is a marked effect on $IgG_3$ content. There is no pH contribution to the effect of Aerosil on subclass distribution.

TABLE 3

The Effect Of Aerosil 200 Concentration Following Extraction Of Supernatant I At pH 7.2 and 5.2.

| | | Subclass Distribution (%) pH | |
| --- | --- | --- | --- |
| Aerosil Conc. | | 7.2 | 5.2 |
| No Aerosil | $IgG_1$ | 54.6 | 52.6 |
|  | $IgG_2$ | 35.5 | 34.1 |
|  | $IgG_3$ | 6.0 | 5.6 |
|  | $IgG_4$ | 3.9 | 3.6 |
| 50 mg/g protein | $IgG_1$ | 4.3 | 55.2 |
|  | $IgG_2$ | 36.3 | 35.7 |
|  | $IgG_3$ | 5.5 | 5.4 |
|  | $IgG_4$ | 3.8 | 3.7 |
| 100 mg/g protein | $IgG_1$ | 54.9 | 55.1 |
|  | $IgG_2$ | 36.0 | 36.3 |
|  | $IgG_3$ | 5.2 | 5.0 |
|  | $IgC_4$ | 3.9 | 3.6 |
| 200 mg/g protein | $IgC_1$ | 55.6 | 56.9 |
|  | $IgG_2$ | 38.4 | 37.1 |
|  | $IgG_3$ | 2.0 | 2.3 |
|  | $IgG_4$ | 4.0 | 3.7 |
| 250 mg/g protein | $IgG_1$ | 5.8 | 57.4 |
|  | $IgG_2$ | 39.0 | 38.0 |
|  | $IgG_3$ | 1.0 | 0.9 |
|  | $IgG_4$ | 4.1 | 3.7 | d. FIG. 1 presents the results of a study examining the effect of Aerosil grade on filterability of Supernatant I. Aerosil 200 or Aerosil 380 at 0.18 g/g protein together with Diacel 150 at 0.3 g/g protein was added to 200 mL of Supernatant I. Following mixing for 30 minutes at 4° C., the suspension was applied to a laboratory scale leaf-filtration apparatus.

Flow was effected with compressed air to 2 bar. When filtrate clarity was attained, flow-rate was monitored. The plot of the data shows that when Aerosil 380 was used complete filtration of the material was achieved by 21 minutes. With Aerosil 200 only approximately 40% of the material had flowed through by this time and flow-rate had slowed down markedly. Complete filtration was not achieved until 224 minutes.

Figure 2:
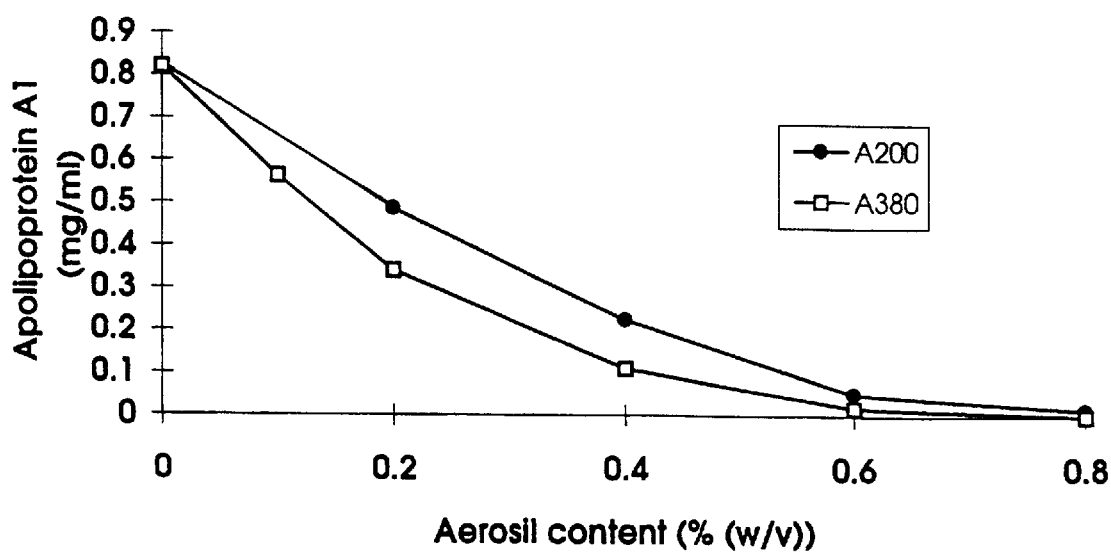
FIG. 2 is a comparison of lipoprotein removal capability from Supernatant I of Aerosil 200 and Aerosil 380.

The capacity of the different grades of Aerosil to remove lipoproteins from Supernatant I was examined. Aerosil 200 or 380 were mixed with Supernatant I at 0.1, 0.2, 0.4, 0.6 and 0.8% (w/v) together with 1.2% (w/v) Diacel. After mixing for 30 minutes at 4° C., the samples were centrifuged and ApolipoproteinA concentration in the supernatant was measured by immunoelectrophoresis. FIG. 2 shows that Aerosil 380 exhibited a greater capacity for lipoprotein removal than Aerosil 200. Between 0.2 and 0.6% Aerosil there was a 30% to 64% improvement in delipidation respectively. At 0.8% Aerosil residual lipoprotein is present after extraction with Aerosil 200 but none was detectable with the use of Aerosil 380. These data indicate that equivalent delipidation to Aerosil 200 can be achieved with less Aerosil 380.

f. in order to further improve the flow-rate of Supernatant I through an Aerosil 380/Diacel bed, the effect of different ratios on flow-rate were examined. As Aerosil 380 exhibits a greater capacity for lipoproteins than Aerosil 200 less can be used. This has the potential to enhance filterability.

Figure 3:
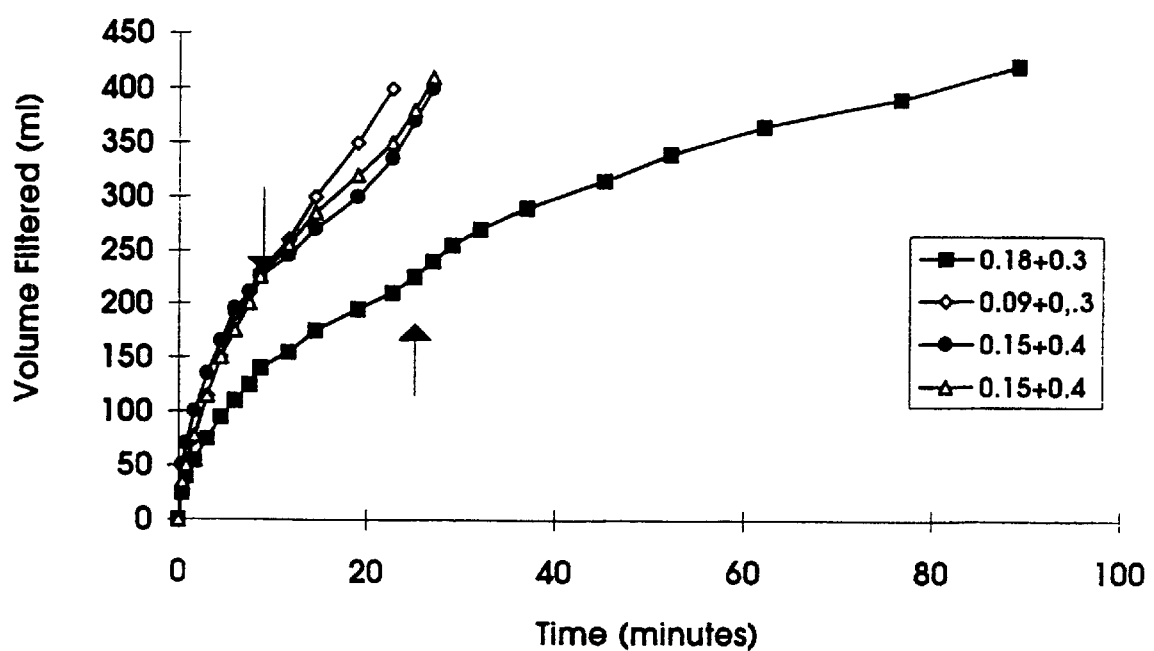
FIG. 3 shows the flow-rate of Supernatant I during leaf-filtration at various ratios of Aerosil 380 to Diacel filter-aid (arrows indicate the start of flushing of the filter cake with 0.4% w/v sodium chloride)

Using the method above for deriving the data described in FIG. 1, Supernatant I was mixed with the following amounts of Aerosil and Diacel:

a. Aerosil 380 0.18 g/g protein, Diacel 0.3 g/g protein
b. Aerosil 380 0.09 g/g protein, Diacel 0.3 g/g protein
c. Aerosil 380 0.15 g/g protein, Diacel 0.4 g/g protein Following passage of the supernatant the filter cake was flushed with 0.4% (w/v) Sodium Chloride. The flow rates achieved are detailed in FIG. 3.

EXAMPLE 2

Generation of a crude immunoglobulin-containing fraction by anion-exchange chromatography using DEAE-Sepharose FF has been investigated as described below.

The effect of the use of 10 mM Sodium Acetate pH 5.2 (0.8 mS/cm) versus 20 mM Sodium Acetate pH5.2 (1.7 mS/cm) on the resolution of proteins in the flow-through fraction recovered from a DEAE-Sepharose FF column was examined.

A 60 mL column of resin (12×2.5 cm) was packed with DEAE-Sepharose. Following equilibration with acetate buffer, delipidated and euglobulin depleted Supernatant I (1.2 mS/cm) was loaded at a flow-rate of 60 cm/hr with an amount equivalent to 40 mg of protein per g of resin. On completion of loading, the column was washed with equilibration buffer until absorption returned to base line. The study was performed at room temperature.

Figure 4:
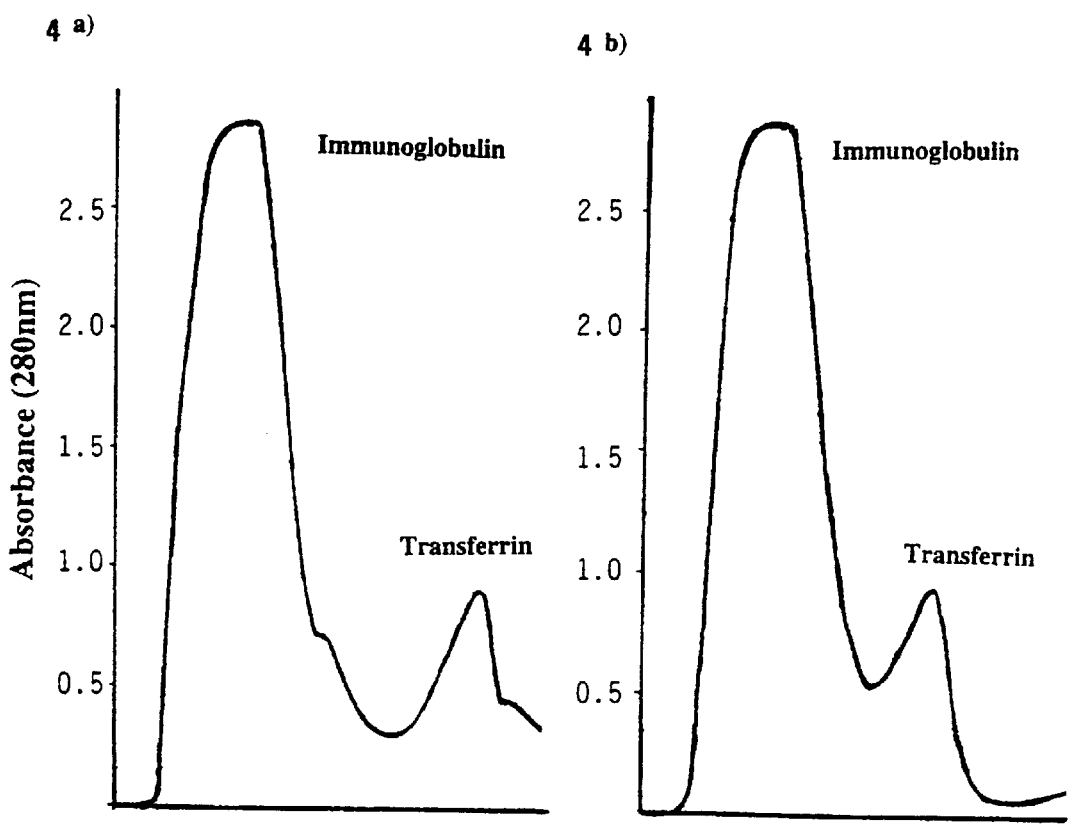
FIG. 4 shows the effect of the ionic strength of the equilibration buffer on the resolution of transferrin from IgG following passage of Supernatant I through DEAE-Sepharose FF equilibrated with (a) 10 mM sodium acetate, pH 5.2 and (b) 20 mM sodium acetate, pH 5.2.
Figure 5:
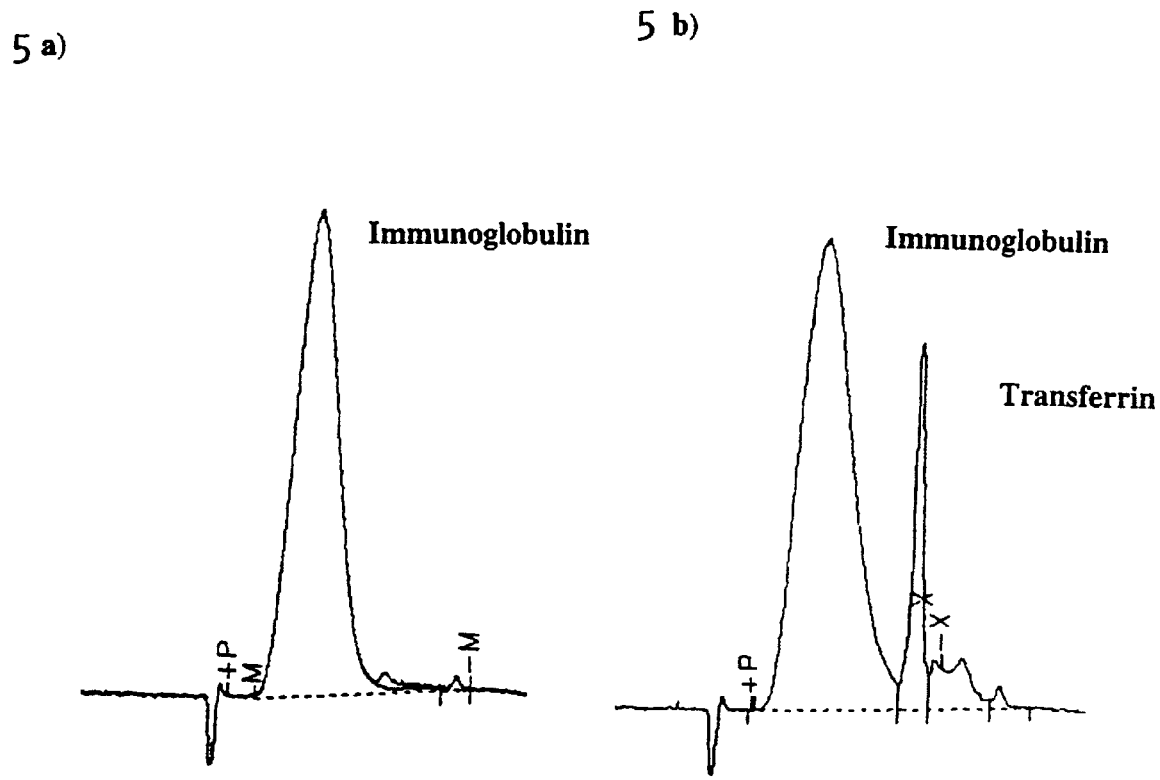
FIG. 5 (FIGS. 5a and 5b) shows the purity of recovered immunoglobulin assessed by capillary electrophoresis following fractionation of Supernatant I on DEAE-Sepharose FF equilibrated with (a) 10 mM sodium acetate, pH 5.2 and (b) 20 mM sodium acetate, pH 5.2.

FIG. 4 illustrates that under low conductivity conditions the resolution of the transferrin peak from immunoglobulin is increased. Analysis of the immunoglobulin peak by capillary electrophoresis revealed a marked improvement in IgG purity at low conductivity due to improved resolution of transferrin (FIG. 5).

EXAMPLE 3

Investigations into optimisation of the second anion-exchange chromatography step for the purification of immunoglobulins are described below.

Figure 6:
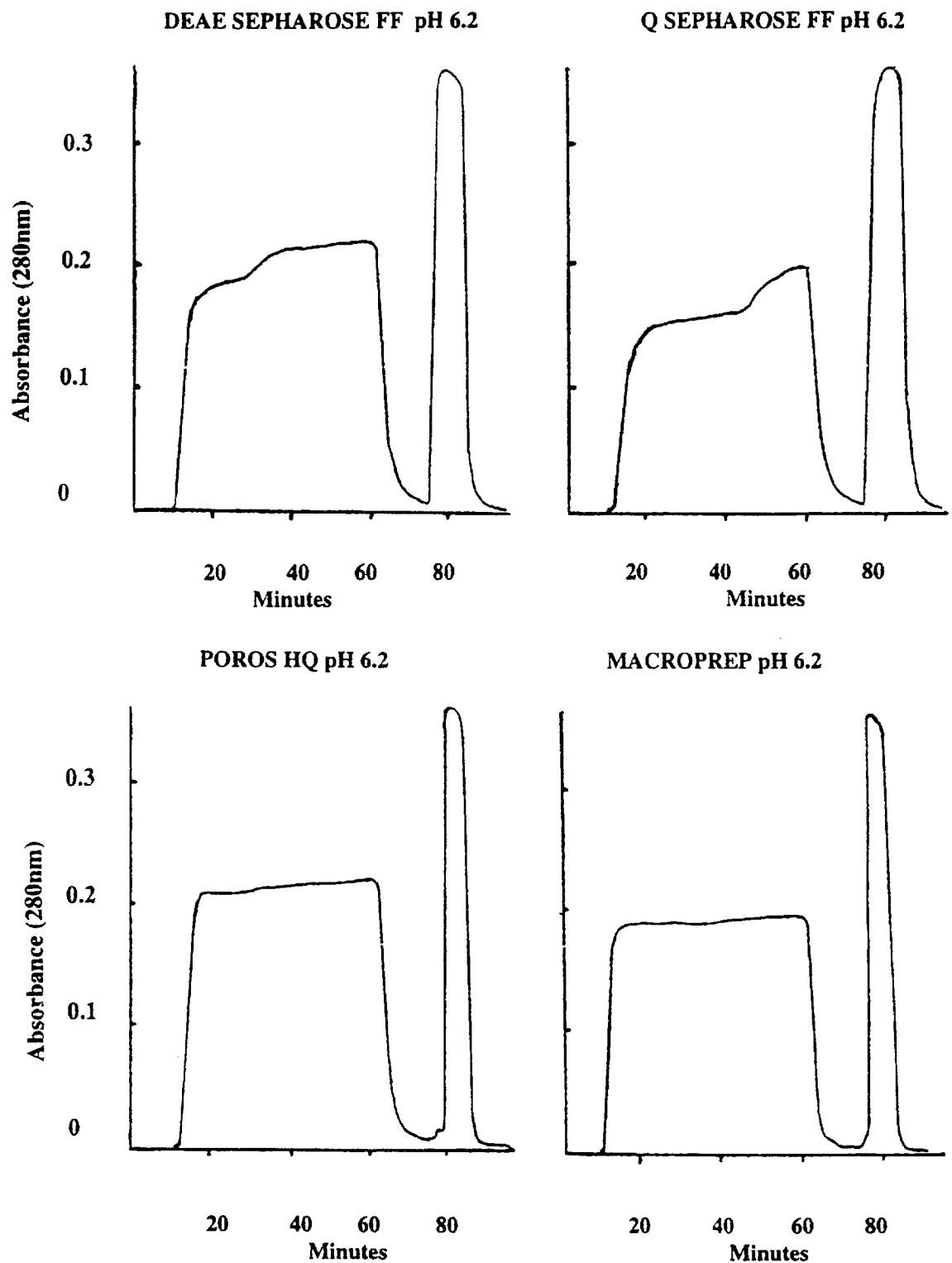
FIG. 6 shows flow-through profiles following loading of crude IgG onto various anion-exchange resins equilibrated with 20 mM sodium acetate, pH 6.2 (Poros HQ, Macro-Prep Q and Q Hyper DM are macro-porous resins; arrows indicate appearance of transferrin in flow-through material)
Figure 6:
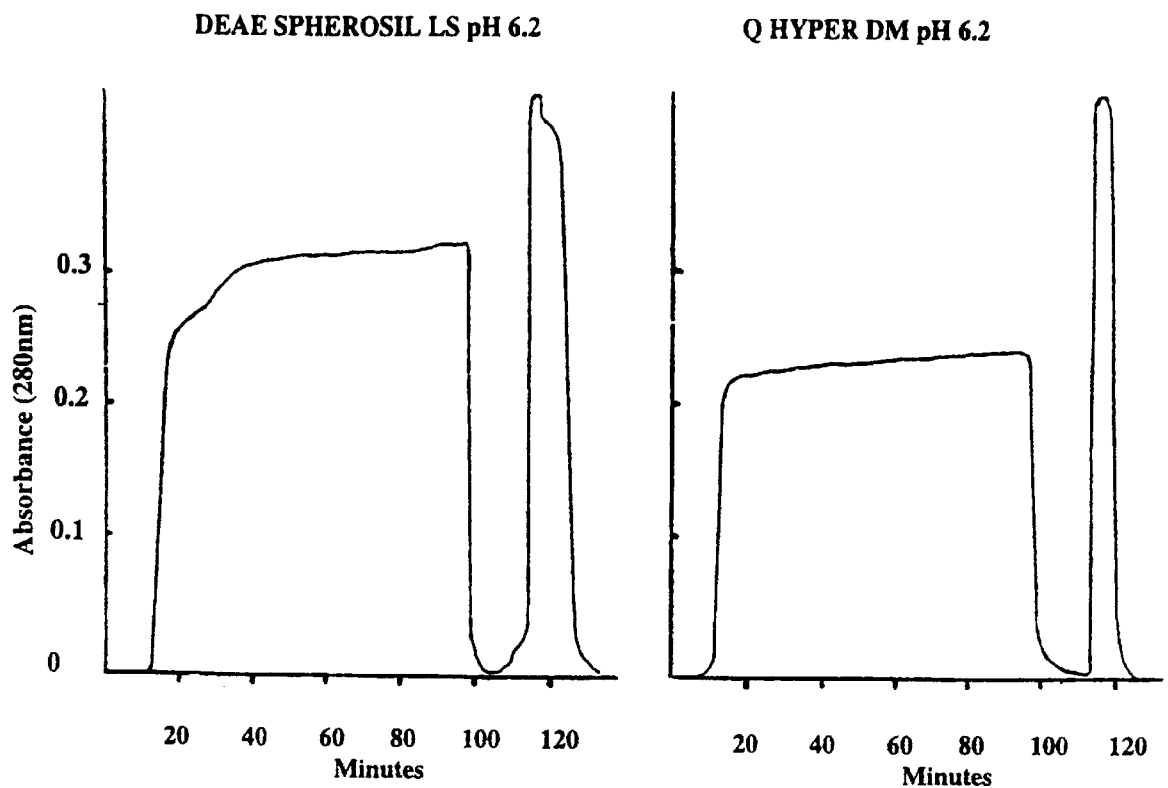

The experiments were performed at a column volume of 60 ml. Loadings were performed at 5 ml/min. The protein concentration of the crude IgG was 5.92 mg/ml. IgG content was 76%.

a. FIG. 6 illustrates that the resins Macro-Prep Q, Poros HQ and Q Hyper DM designated as macro-porous, exhibit a flat drop-through profile reflecting only immunoglobulin flow-through and retention of transferrin. With the other resins an earlier drop-through of transferrin occurred as indicated by a further increase in adsorption above that attributable to immunoglobulin flow-through.

It has been identified that the improved performance of the macro porous resin overcomes the limitations of non-macroporous resins as suggested by the van Dempter equation. The equation identifies that resin performance reflects mass transfer from mobile phase through the stagnant phase to the stationary phase. In resins of low pore size diffusion is the main mechanism of transfer of solute. This is a slow process and can result in insufficient mass transfer. In macro-porous resins there is significant intraparticle flow and solute is efficiently transferred to the stationery phase by convective flow.

b. Further optimisation work was undertaken with Macro-Prep HQ to examine the parameters which maximise the capability of the resin to remove contaminating proteins and in particular transferrin from a crude IgG preparation.

Flow-through experiments showed that for adequate retention of transferrin to occur chromatography on Macro-Prep HQ should be undertaken at greater than pH 6.0

A specific example is presented in Table 5 comparing the retention of transferrin by MacroPrep HQ at pH 6.2 and 6.5 and illustrates the pH effect on transferrin adsorption. Resin was packed to 10 ml in columns and equilibrated with 10 mM Sodium Acetate buffer at pH 6.2. Crude IgG adjusted to pH 6.2 and 6.5 at a concentration of 3.4 mg/ml and containing 0.41 mg/ml of transferrin was loaded at 3.5 ml/min.

TABLE 5

The Effect Of pH On Transferin Drop-Through Following Loading of a Crude IgG Preparation onto Macro-Prep HQ.

| Volume of Crude IgG loaded (ml) | Conc. of Transferrin | |
|---|---|---|
| | pH 6.2 Transferrin (mg/mL) | pH 6.5 Transferrin (mg/mL) |
| 28 | Nil | Nil |
| 40 | Nil | Nil |
| 52 | .0185 | Nil |
| 60 | .0185 | Nil |
| 77 | .0234 | Nil |
| 84 | .0234 | Nil |
| 96 | .0286 | Nil |

The effect of temperature on the capacity of Macro-Prep HQ for transferrin was examined. A 10 mL column of resin was packed with Macro-Prep HQ (1.6×5 cm) and equilibrated 10 mM Sodium Acetate pH 6.5. Crude IgG containing 3.1 mg/ml of transferrin was loaded at a flow rate of 3.5 ml/min at 4° C. and 15° C. Transferrin concentrations in the drop-through fractions were determined by immunoelectrophoresis.

Figure 7:
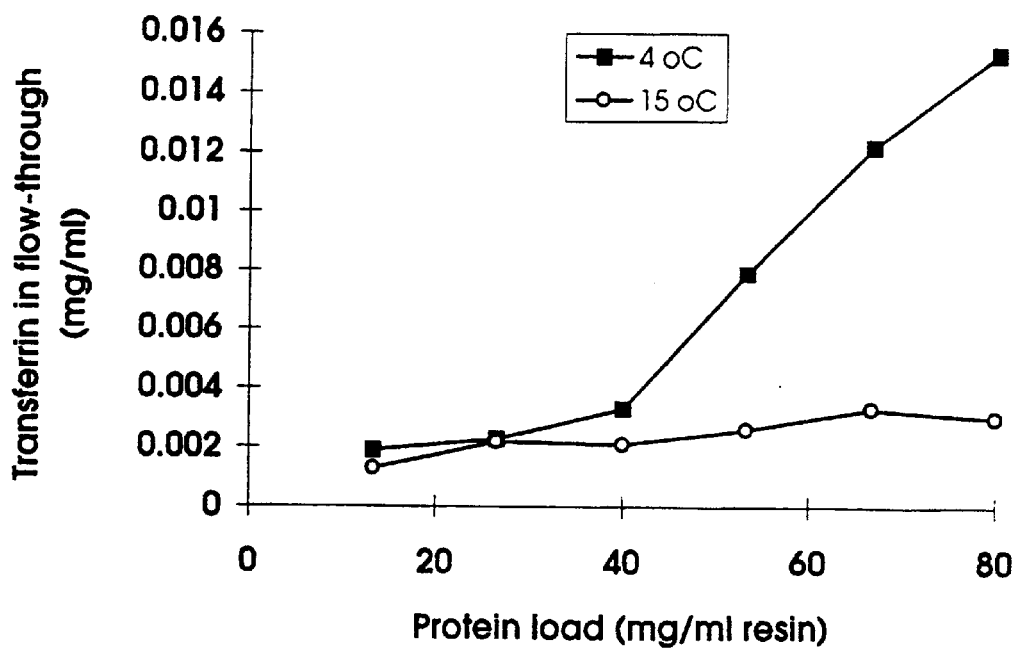
FIG. 7 shows the effect of temperature on transferrin drop-through following the loading of crude IgG containing transferrin onto Macro-Prep HQ resin.

FIG. 7. shows that as the loading of the resin increases, a temperature effect becomes evident, with an increased capacity for transferrin evident at 15° C.

Figure 8:
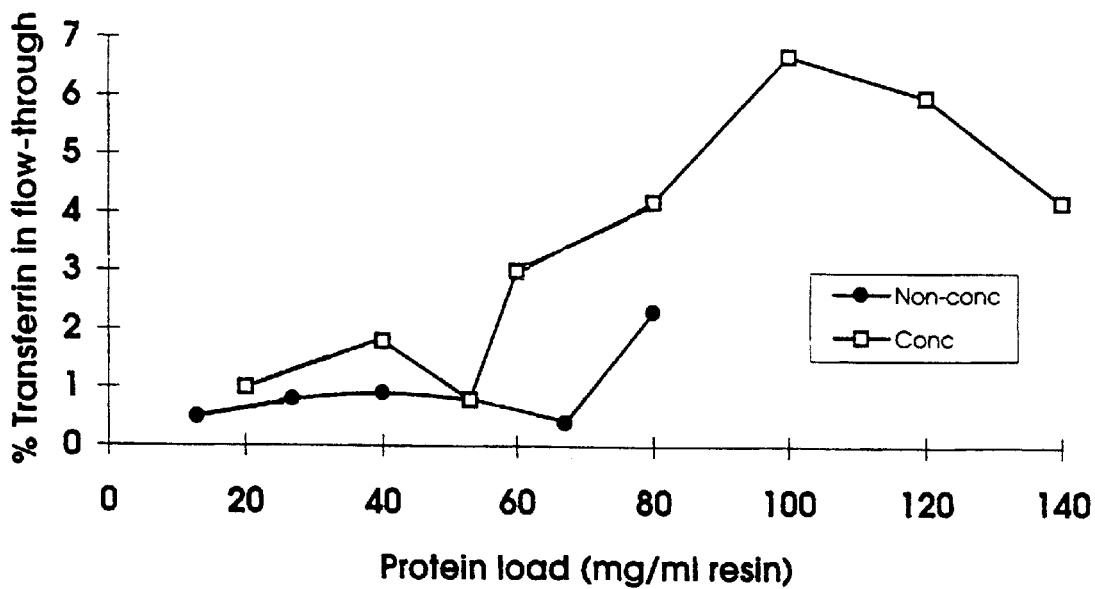

FIG. 8. shows the drop-through of transferrin is a function of the protein concentration of the crude IgG preparation loaded onto the resin. The data shown was obtained by the procedure described above to examine the effect of tempre-rature. The protein concentration of the concentrated and dilute crude IgG was 18 and 3 mg/ml respectively. The transferrin concentration in the corresponding samples was 3.1 and 0.51 mg/ml.

Figure 9:
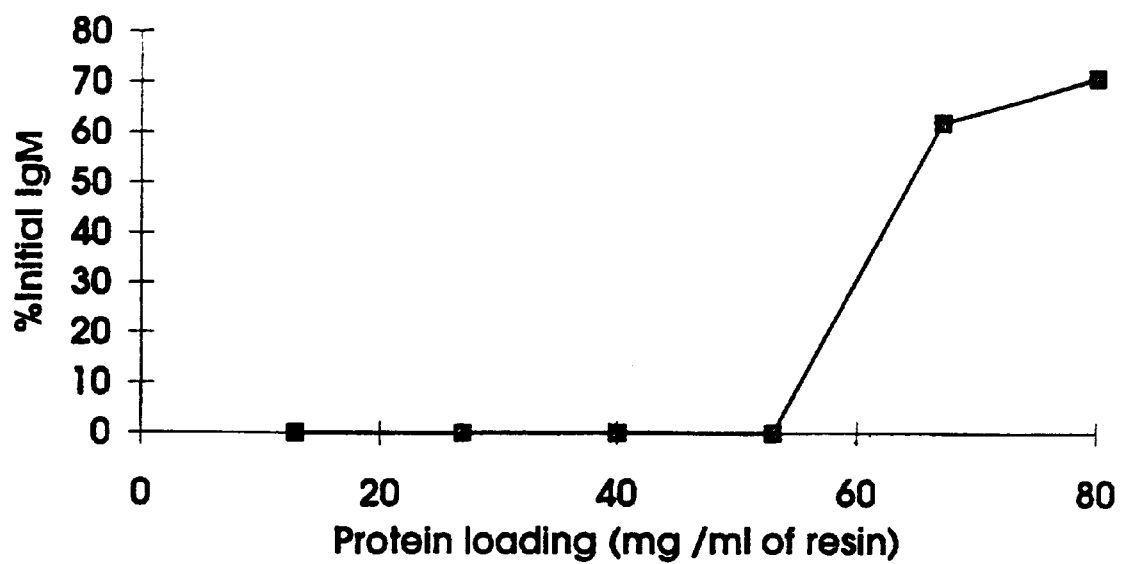

Transferrin was analysed in the drop-through fractions by immunoelectrophoresis. Fractions from the loading of dilute material were concentrated 6–10 fold, before analysis. It can be seen that when crude IgG is loaded in dilute form, there is greater retention of transferrin by the resin when compared to equivalent loadings with concentrated crude IgG. Thus the transferrin concentration in the drop-through fractions is less than 1% of the transferrin concentration present in the crude IgG after loading of 67 mg of crude IgG/ml of resin in a dilute form. However when crude IgG is loaded in a concentrated form a 1% drop-through of transferrin is evident at a loading of 20 mg/ml. These results indicate that the concentration of crude IgG loaded onto the Macro-Prep resin can significantly can significantly affect the capacity of the resin for transferrin.

e. FIG. 9 also shows data for the effect of the degree of loading of crude IgG onto Macro-Prep HQ on IgM drop-through. The crude IgG was loaded in non-concentrated form. It can be seen that if more than 53 mg of crude IgG per mL of resin are applied to Macro-Prep resin a significant increase in IgM flow-through occurs.

EXAMPLE 4

Chromatographic Purification of IgG Derived from Fraction II+III.

This example illustrates the capability of the chromatographic conditions described to produce purified IgG from resolubilised Fraction II+III. The resolubilisation process may be carried out as follows. Starting material IgG enriched Fraction II+III, which is derived from human plasma using the Cohn method of plasma protein fractionation, was solubilised at 0–4° C. with buffers at a pH range of 4.0 to 8.4 and a conductivity of 0.9 to 14.0 mS/cm. The buffers used may include 0.025M Tris-HCl pH8.4 and 0.02M sodium acetate from pH4 to 5.2. The volume of buffer for resolubilisation of Fraction II+III paste may range from 5–30 ml/g of paste. The typical yields, purity and subclass distribution of IgG derived from resolubilised Fraction II+III are shown in Table 6.

TABLE 6

Recovery and characteristics of IgG derived from Fraction II + III with various solubilisation regimens +.

| Buffer | Vol. (ml) | Total protein (mg) | Total IgG (mg) | IgG yield (%)* | IgG purity (%) | IgG Subclasses (%) IgG1/IgG2/IgG3/IgG4 |
|---|---|---|---|---|---|---|
| 0.025 M Tris pH 8.4 | 5–30 | 138–163 | 52–66 | 57–65 | 36–44 | 50.9/35.1/6.2/7.8 |
| 0.02 M Sodium acetate pH 5.2 | 5–30 | 77–119 | 51–73 | 51–73 | 50–66 | 53.5/35.2/5.6/5.6 |
| 0.02 M Sodium acetate pH 4.5 | 5–30 | 110–125 | 55–61 | 59–62 | 46–55 | 53.4/34.8/5.7/6.1 |
| 0.02 M Sodium acetate pH 4.0 | 5–30 | 96–129 | 46–62 | 47–70 | 49–56 | 51.8/31.8/8.8/7.6 |

*IgG yields are calculated by dividing the amount of IgG recovered with the total amount of IgG present in the Fraction II + III. Total IgG values in Fraction II + III were determined by densitometric scanning of samples run on SDS-PAGE gels.
+ Data represents the range of results obtained with different resolubilisation regimens.

The table indicates that substantial yields of IgG (60%) are recovered with maximal enrichment using the buffer 0.02M sodium acetate pH 5.2 in the ratio of 10–25 ml/g of paste. At this pH, a significant amount of non-IgG protein remained insoluble. Subclass analysis studies indicated that the distribution in resolubilised IgG was comparable to that of published plasma values.

The solubilised Fraction II+III solution was clarified by passage through a Lochem filtration apparatus following the addition of Diacel. The recovered solutions was further clarified by filtration through a 1.2 μm filter (Millipore). The use of Aerosil to delipidate the solution was not necessary as the lipoprotein content of resolubilised Fraction II+III was found to be low.

For the chromatographic purification of the recovered resolubilised IgG, a Macro-Prep HQ (Bio-Rad) column (Pharmacia XK26/20, bed volume 60 mls) was prepared and equilibrated with 0.02M sodium acetate pH 6.2. The protein solution (volume 660 mls, total protein 6.2 g) was adjusted to pH 6.5 and diluted with PFW to a conductivity value equal to that of the equilibrating buffer (2.7 mS/cm). The solution was then filtered through 5 μm and 0.5 μm filters (Millipore) and loaded onto the column at a flow rate of 5 ml/min. The chromatography was performed at 20–25° C. The recovery of successive pooled fractions and associated subclass distribution of IgG obtained following this treatment is shown in Table 7.

TABLE 7

Recovery of IgG following purification of Fraction II + III purified by Macro-Prep HQ chromatography.

| SAMPLE | Vol. fract. (ml) | Total IgG (mg) | IgG SUBCLASS DISTRIBUTION % | | | |
|---|---|---|---|---|---|---|
| | | | IgG1 | IgG2 | IgG3 | IgG4 |
| Pre-Macro-Prep HQ | 660 | 4229 | 52.4 | 35.1 | 6.3 | 6.3 |
| Fraction 1–20 | 170 | 899.3 | 59.3 | 33.3 | 6 | 1.4 |

TABLE 7-continued

Recovery of IgG following purification of Fraction II + III purified by Macro-Prep HQ chromatography.

| SAMPLE | Vol. fract. (ml) | Total IgG (mg) | IgG SUBCLASS DISTRIBUTION % | | | |
|---|---|---|---|---|---|---|
| | | | IgG1 | IgG2 | IgG3 | IgG4 |
| Fraction 21–41 | 210 | 1194.9 | 57.1 | 34.1 | 6.8 | 2 |
| Fraction 42–62 | 210 | 1304.1 | 55.9 | 34 | 6.7 | 3.4 |
| Fraction 63–80 | 100 | 372 | 53 | 34 | 7.3 | 5.7 |
| Recovery % | | 89.2 | | | | |

Capillary electrophoresis studies on all pooled fractions indicated that the IgG recovered was homogeneous.

This example thus demonstrates a practical process by which IgG can be resolubilised from Fraction II+III and purified to homogeneity by a single chromatographic step.

References

Berglof J. H., Eriksson S. E. (1989), Plasma Fractionation by Chromatography of Albumin and IgG. In: Biotechnology of Plasma Protein. Stoltz J. F., Rivat C. Eds. Colloque INSERM 175 201–206.

Björling H. (1972), Plasma Fractionation Methods used in Sweden. Vox.Sang 23 18–25.

Bjorling H., (1985), A New Protein Fractionation Method Using Ion-Exchange Chromatography and PEG *Precipitation.* Vox.Sang 49 240–243.

Cohn E. J., Strong L. E., Hughes W. L. jr, Mulford D. J., Ashworth J. N., Melin M. and Taylor H. L. (1946), Preparation and Properties of Serum and Plasma Proteins IV. A system for the separation into fractions of the protein and lipoprotein components of biological tissues and fluids. *J. Am. Chem. Soc.* 68 459–475.

Condie R. M. (1979), A preparation of Intravenous Human and Animal Gamma Globulins and isolation of Albumin. (U.S. Pat. No. 4,136,094).

Condie R. M. (1980), Preparation and Intravenous Use of undenatured Human IgG. In: Immunoglobulin: Characterisation and Uses of Intravenous Preparations U.S. Dept. of Health and Human Services, Public Health Services FDA. pp 179–194.

Friesen A. D.(1982), Process for Preparing Purified Immune Globulin (IgG), Canadian Patent Application No. 407, 649.

Friesen A. D., Bowman J. M. and Bees W. C. H. (1985) Column Ion Exchange Chromatographic Production of Human Immune Serum Globulin for Intravenous Use. *Vox.Sang* 48 201–212.

Hoppe H. H., Mester T., Hennes W. and Krebs J. J. (1973) Prevention of Rh Immunization: Modified Production of IgG Anti-Rh for Intravenous Application by Ion-exchange Chromatography. *Vox.Sang* 25 308–316.

Tousch D., Allary M., Saint-Blancard J. and Boschetti E. (1989), Preparative Purification of IgG from a Human Plasma Alcohol Precipitate, In: Biotechnology of Plasma Protein. Stoltz J. F., Rivat C. Eds. Colloque INSERM 175 229–236

Samo M. E. (1991), Process for Purifying Immune Serum Globulins, European Patent Application No. 91300790.2.

What is claimed is:

1. A method for the purification or recovery of immunoglobulins from plasma or other immunoglobulin-containing material, which comprises the step of subjecting the plasma or other immunoglobulin-containing material to chromatographic fractionation on a macro-porous anion-exchange resin to recover an immunoglobulin-containing fraction therefrom, wherein said macro-porous anion exchange resin has a pore size of greater than 1000 Å and wherein said chromatographic fractionation is carried out at a pH of 6.0 to 6.6.

2. A method according to claim 1, wherein said chromatographic fractionation is carried out at a conductivity of 0.7 to 1.5 mS/cm.

3. A method according to claim 1, wherein the plasma or other immunoglobulin-containing starting material contains lipoproteins, and wherein said lipoproteins are removed by adsorption prior to said chromatographic fractionation.

4. A method according to claim 3, wherein said lipoproteins are adsorbed on a finely divided silicon dioxide adsorbent to produce delipidated material.

5. A method according to claim 4, wherein said finely divided silicon dioxide adsorbent has a particle size in the range of from 5 to 50 nm.

6. A method according to claim 4, wherein said adsorption of lipoproteins is carried out at a pH of 5.2 to 7.2.

7. A method according to claim 4, wherein said adsorption of lipoproteins is carried out at a conductivity of 6 to 12 mS/cm.

8. A method according to claim 4, wherein the silicon dioxide adsorbent having lipoproteins adsorbed thereto is removed by filtration, preferably in the presence of a filter-aid.

9. A method according to claim 4, wherein said delipidated material is fractionated by anion-exchange chromatography to produce a first immunoglobulin-containing fraction, priorto said chromatographic fractionation on a macro-porous anion-exchange resin.

10. A method according to claim 9, wherein said delipidated material is diafiltered, pH adjusted and euglobulin depleted prior to said fractionation by anion-exchange chromatography.

11. A method according to claim 10, wherein said fractionation of said delipidated, euglobulin depleted material is carried out at pH 5.2 and a conductivity of 0.5 to 1.0 mS/cm.

12. A method according to claim 1, wherein said immunoglobulin-containing material is plasma.

13. A method according to claim 1, wherein said immunoglobulin-containing material is a plasma fraction obtained by the Cohn fractionation process.

14. A method according to claim 13, wherein said plasma fraction is Cohn Supernatant I.

15. A method according to claim 13, wherein said plasma fraction is resolubilised Fraction II+III.

16. A method according to claim 1, wherein said chromatographic fractionation on a macro-porous anion-exchange resin is carried out at a temperature of between 4 and 20° C.

17. A method according to claim 1, wherein said chromatographic fractionation on a macro-porous anion-exchange resin is carried out using a protein concentration of less than about 3 mg/ml.

18. A method according to claim 1, wherein said chromatographic fractionation on a macro-porous anion-exchange resin is carried out using a loading of immunoglobulin-containing material not exceeding about 50 mg/ml of macro-porous resin.

19. A method according to claim 1, wherein the purified immunoglobulin-containing fraction is subjected to viral inactivation.

20. A method according to claim 19, wherein said viral inactivation comprises a pasteurisation step.

* * * * *